United States Patent
Fukunaga

[19]

[11] Patent Number: 6,066,298
[45] Date of Patent: May 23, 2000

[54] PRETREATMENT APPARATUS

[75] Inventor: Shingo Fukunaga, Yamaguchi, Japan

[73] Assignee: Tosoh Corporation, Yamaguchi, Japan

[21] Appl. No.: 08/832,670

[22] Filed: Apr. 4, 1997

[30] Foreign Application Priority Data

Apr. 4, 1996 [JP] Japan ................... 8-082541

[51] Int. Cl.$^7$ ............... B08B 9/00; B08B 3/04
[52] U.S. Cl. ............... 422/100; 422/62; 422/63; 422/99; 422/104; 134/170
[58] Field of Search ............... 422/62, 63, 66, 422/67, 68.1, 70, 99, 100, 101, 102, 103, 104; 134/170

[56] References Cited

U.S. PATENT DOCUMENTS

| | | | |
|---|---|---|---|
| 3,192,968 | 7/1965 | Baruch et al. | 141/82 |
| 4,451,433 | 5/1984 | Yamashita et al. | 422/63 |
| 4,495,149 | 1/1985 | Iwata et al. | 422/65 |
| 4,574,850 | 3/1986 | Davis | 141/9 |
| 4,730,631 | 3/1988 | Schwartz | 134/155 |
| 4,820,497 | 4/1989 | Howell | 422/63 |
| 4,946,651 | 8/1990 | Liston et al. | 422/102 |
| 4,948,563 | 8/1990 | Kanewske, III | 422/99 |
| 5,558,838 | 9/1996 | Uffenheimer | 422/100 |
| 5,679,575 | 10/1997 | Kubota et al. | 436/49 |

FOREIGN PATENT DOCUMENTS

| | | |
|---|---|---|
| 0299419 | 7/1988 | European Pat. Off. . |
| 0 299 419 | 1/1989 | European Pat. Off. . |
| 0 388 018 | 9/1990 | European Pat. Off. . |
| 0 472 213 | 2/1992 | European Pat. Off. . |
| 0 661 542 | 7/1995 | European Pat. Off. . |
| 2 629 207 | 7/1988 | France . |

OTHER PUBLICATIONS

Tanya Duncan et al., The Boehringer Mannheim ES 300 Immunoassay System, vol. 14, No. 2, journal of Clinical Immunoassay, pp. 105–110, Jun. 8, 1991.

*Primary Examiner*—Lyle A. Alexander
*Attorney, Agent, or Firm*—Sughrue, Mion, Zinn, Macpeak & Seas, PLLC

[57] ABSTRACT

It is an object to provide an apparatus adaptable to an apparatus for analyzing liquid samples in the chemical field or the biochemical field, and capable of performing pretreatment, such as washing of the needle and diluting of the collected sample. The pretreatment apparatus comprising: a needle for sampling at least a liquid sample in a predetermined quantity which must be pretreated; a needle holding mechanism for movably holding the needle in a vertical direction; a frame for movably holding the needle holding mechanism in a horizontal direction; a needle washing block which is provided for the needle holding mechanism, which is capable of moving in the horizontal direction together with the needle and the vertical movement of which is inhibited; a pretreatment tank formed by integrating a diluting tank for diluting the liquid sample and a liquid discharge tank for discharging waste liquid; a mixing fluid passage for mixing the diluted liquid sample; and pipes and at least two syringes for defining flow passages connecting the needle, the needle washing block, the pretreatment tank, and the mixing fluid passage.

7 Claims, 3 Drawing Sheets

FIG. 3a
FIG. 3b
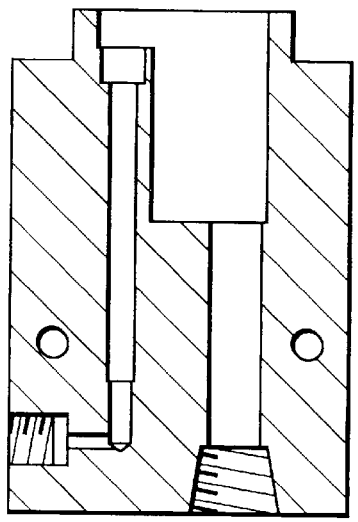
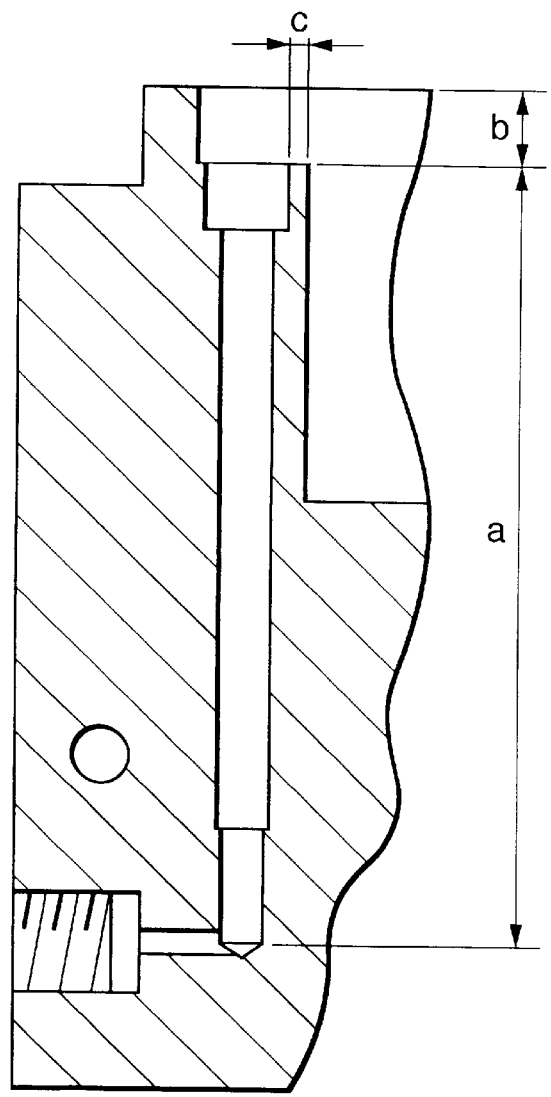

PRETREATMENT APPARATUS

BACKGROUND OF THE INVENTION

The present invention relates to an apparatus for analyzing a liquid sample for use in the chemical field and the biochemistry field, and more particularly to an apparatus for performing pretreatment, such as washing of a needle or dilution of the collected sample.

For example, analysis of glycated hemoglobin using, for example, liquid chromatography has been performed such that a blood sample in a tube (a vacuum blood collecting tube) having a rubber cap is collected in a predetermined quantity to analyze the quantity of glycated hemoglobin component in the sample.

The foregoing operation is specifically performed such that a pin type needle capable of penetrating the rubber cap of the vacuum blood collecting tube is caused to accurately penetrate a penetration target portion having a diameter of about 5 mm in the central portion of the rubber cap to collect a blood sample in a predetermined quantity, and then the blood sample is diluted into an arbitrary dilution ratio, followed by introducing the blood sample into an analysis column. Therefore, pretreatment including collection (sampling) and dilution must be performed before the sample is actually supplied to the column. When analysis of glycated hemoglobin is performed, another pretreatment for hemolyzing red blood cells must be performed before the sample is supplied to the analyzing column. To sequentially analyze a plurality of blood samples, pretreatment of washing the needle must be performed before the operation is performed.

As described above, various analyzing apparatuses including the glycated-hemoglobin analyzing apparatus, have the structure to control the component parts thereof to cause the components parts to perform complicated operations. Moreover, special parts for washing and dilution have been provided.

The pretreatment will now be described with reference to FIG. 1 such that an apparatus for analyzing blood, such as the glycated-hemoglobin analyzing apparatus, is taken for example. The glycated-hemoglobin analyzing apparatus is required to be capable of sucking the blood sample from the vacuum blood collecting tube having the rubber cap with satisfactory reproducibility, removing contamination occurring due to carrying of the sample and having excellent dilution reproducibility about, in general, 200 times to about 400 times.

Initially, a needle 1 is moved to a sampling position 2, and then a rubber cap is caused to penetrate a vacuum blood collecting tube 3 having the rubber cap to be moved downwards. Thus, a blood sample is sucked in a predetermined quantity attributable to the reciprocating operation of a first syringe 4. To suck the blood sample with satisfactory reproducibility, the foregoing predetermined quantity must be 3 microliter or greater. In order to cause the first syringe 4 to perform the sucking operation, a first valve 5 is closed.

Then, the needle is moved to a dilution tank 6 to discharge the sucked blood sample, and then a second syringe 7 is operated to jet out solution (diluting solution) from a dilution nozzle 8 in a predetermined quantity so as to dilute the blood sample to a predetermined dilution ratio (in general, 200 times to 400 times). After jetting of the solution from the dilution nozzle 8 has been completed, the first valve and the second valve 9 are switched to introduce the diluted sample into a sample injector 10 formed by using a hexagonal valve. Then, the diluted sample is supplied to the analyzing column. To also perform the dilution operation with excellent reproducibility, the quantity of the collected blood sample must be 3 microliter or greater.

After the foregoing operations have been completed, the dilution chamber and the needle are washed in order to analyze a new blood sample. The needle is washed by a method in which solution is allowed to flow in a needle washing block 11 by a washing pump 12 or a method in which washing solution is discharged from the needle in a needle washing tank 13, and then a third valve 14 is opened and a suction pump 15 is operated so as to suck the contaminated washing solution into a vacuum chamber 16 followed by opening a fourth valve 17 at a certain timing so as to discharge the contaminated solution into a discharge portion 18.

The dilution tank 6 is washed such that the washing solution is discharged from the needle 1 or the dilution nozzle 8 into the dilution tank until the tank is fully filled with the solution. Then, a fifth valve 19 is opened, and then the suction pump 15 is operated so as to suck the contaminated washing solution into the vacuum chamber 16, followed by opening the fourth valve 17 at a certain timing so as to discharge the contaminated solution into the discharge portion 18.

To reduce the contamination occurring between the samples, the needle 1, the needle washing tank 13, the needle washing block 11, the dilution tank 6, the sample injector 10 and the inside portions of the pipes for establishing the connections among foregoing components must be washed.

The glycated-hemoglobin analyzing apparatus and the like, and particularly, the conventional analyzing apparatus for treating liquid samples, such as blood samples, must suck the blood sample from the vacuum blood collecting tube in a quantity of 3 microliter or more in order to improve the reproducibility. Since the dilution ratio of a usual blood sample is 200 times to 400 times, the capacity of the dilution tank must be 1500 microliter or greater. As a result, there arises a problem in that a large quantity of washing solution not smaller than about 3000 microliter is required to perform the washing operation.

Moreover, the conventional apparatus must be provided with the exclusive suction pump and the exclusive valve for washing the dilution tank. Moreover, the exclusive solution supply pump and an exclusive valve are required to wash the needle. As a result, the structure of the apparatus becomes too complicated and operation of each component becomes too complicated. As a result, a long time is required to perform the pretreatment.

The conventional apparatus shown in FIG. 1 involves the structure such that the dilution tank 6 is fully filled with the washing solution discharged from the needle 1 or the dilution nozzle 8 followed by opening the fifth valve 19 to perform sucking. Therefore, the upper end portion of the dilution tank cannot be washed sufficiently and thus the probability of the occurrence of contamination cannot be eliminated. According to circumstances, there arises a problem in that the needle or the valve is clogged. Therefore, complicated maintenance must be performed such that the dilution tank 6, the valve 19 and the suction pump 15 must periodically removed from the apparatus so as to be manually washed.

In particular, in the case of the vacuum blood collecting tube having the rubber cap, the needle penetrates the rubber cap. Therefore, there is a possibility that abrasion dust of the rubber cap allowed to adhere to the needle scatters into the apparatus. In this case, there arises a problem in that the overall passage, which reaches the analyzing column, is clogged.

After the liquid sample has been sucked, the needle is moved into the dilution tank, and then the diluting solution is discharged from the dilution nozzle to realize an arbitrary dilution ratio (200 times to 400 times). At this time, the diluting solution is jetted out into the dilution tank from a diagonally upward direction deviated from the center of the dilution tank so as to generate a swirl in the dilution tank in order to improve the dilution efficiency. However, since the quantity of the jetted diluting solution is determined by the solution ratio, there arises a problem in that the blood sample and the diluting solution cannot sufficiently be mixed if the solution ratio is low.

If a liquid sample is a sample of blood, the pretreatment sometimes includes the operation for hemolyzing blood in addition to the dilution operation. However, only the foregoing dilution operation easily results in unsatisfactory degree of the hemolysis.

SUMMARY OF THE INVENTION

It is an object of the present invention to provide a pretreatment apparatus overcoming the aforementioned problems experienced with the conventional technology. The object according to the present invention can be achieved by a pretreatment apparatus comprising:

a needle for sampling at least a liquid sample in a predetermined quantity which must be pretreated;

a needle holding mechanism for movably holding the needle in a vertical direction;

a frame for movably holding the needle holding mechanism in a horizontal direction;

a needle washing block which is provided for the needle holding mechanism, which is capable of moving in the horizontal direction together with the needle and the vertical movement of which is inhibited;

a pretreatment tank formed by integrating a diluting tank for diluting the liquid sample and a liquid discharge tank for discharging waste liquid;

a mixing fluid passage for mixing the diluted liquid sample; and pipes and at least two syringes for defining flow passages connecting the needle, the needle washing block, the pretreatment tank, and the mixing fluid passage.

The pretreatment apparatus according to the present invention has the structure such that when the diluted sample which has diluted the liquid sample, such as blood, is larger than the capacity of the dilution tank, the portion exceeding the foregoing capacity is caused to flow over into the solution discharge tank so as to be abolished. When usual glycated-hemoglobin analysis must dilute the blood sample by 200 times to 400 times. On the other hand the quantity of the blood sample to be collected cannot be made to be 3 microliter or smaller to obtain satisfactory reproducibility. As a result, if the overall quantity of the diluted sample is stored, the capacity of the dilution tank is enlarged, causing the washing solution to be required in a large quantity to wash the dilution tank. What is worse, the diffusion and mixture of the blood sample in the dilution tank are frequently insufficient. On the other hand, the present invention has the structure such that the capacity of the dilution tank is positively made to be small and the diluted sample allowed to flow over the dilution tank is used to perform primary washing of the dilution tank.

BRIEF DESCRIPTION OF THE DRAWINGS

FIGS. 3(a) and 3(b) are diagrams showing a pretreatment tank formed by integrating a dilution tank for diluting a liquid sample and a solution discharge tank for use in the embodiment of the present invention, in which FIG. 3a shows the overall structure of the pretreatment tank and FIG. 3b shows only the dilution tank.

DETAILED DESCRIPTION OF THE PREFERRED EMBODIMENT

The apparatus according to an embodiment of the present invention applied as a pretreatment portion of a glycated-hemoglobin analyzing apparatus will now be described in detail with reference to the drawings.

Figure 1:
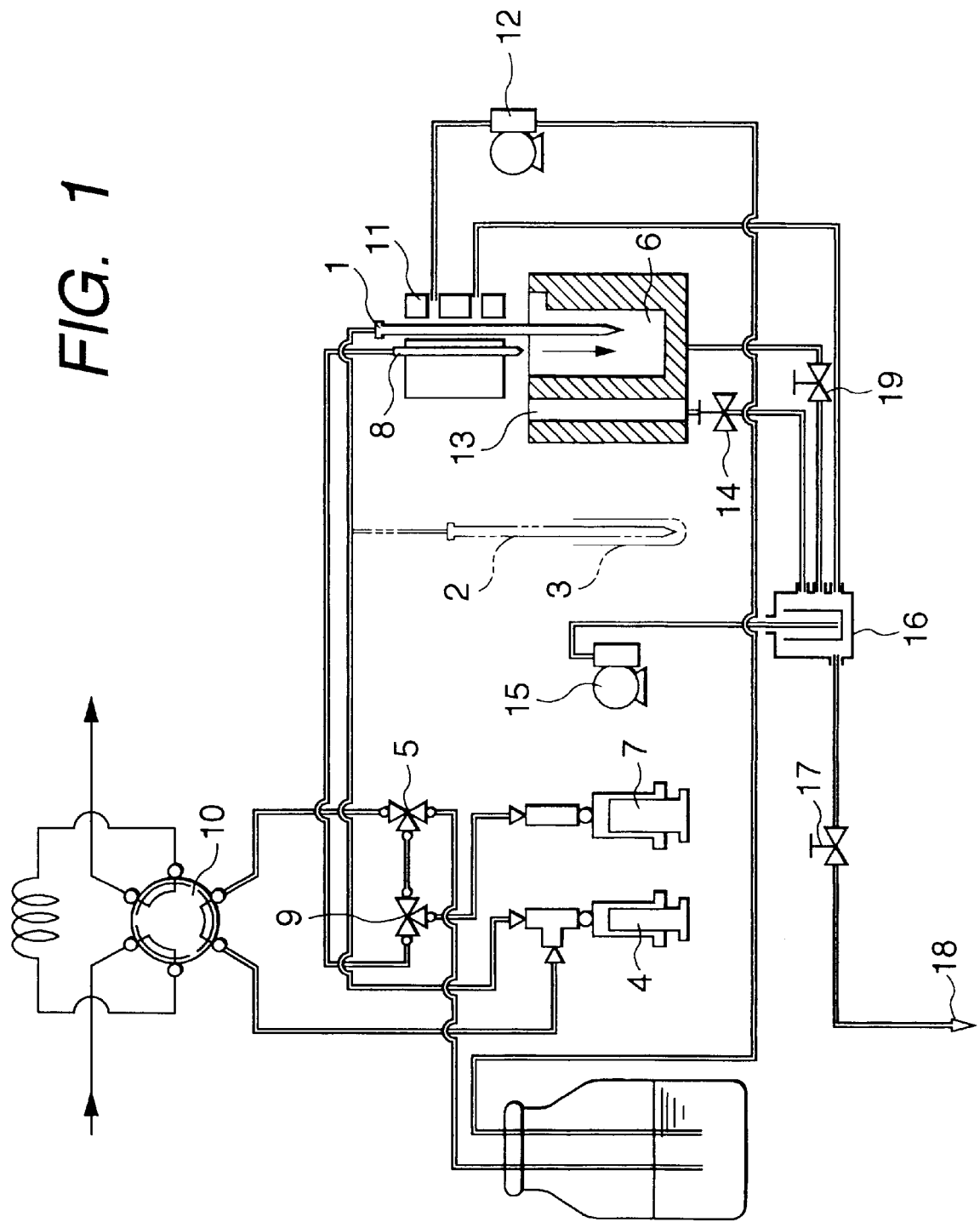
FIG. 1 is a diagram showing a conventional pretreatment apparatus applied to a glycated-hemoglobin analyzing apparatus.
Figure 2:
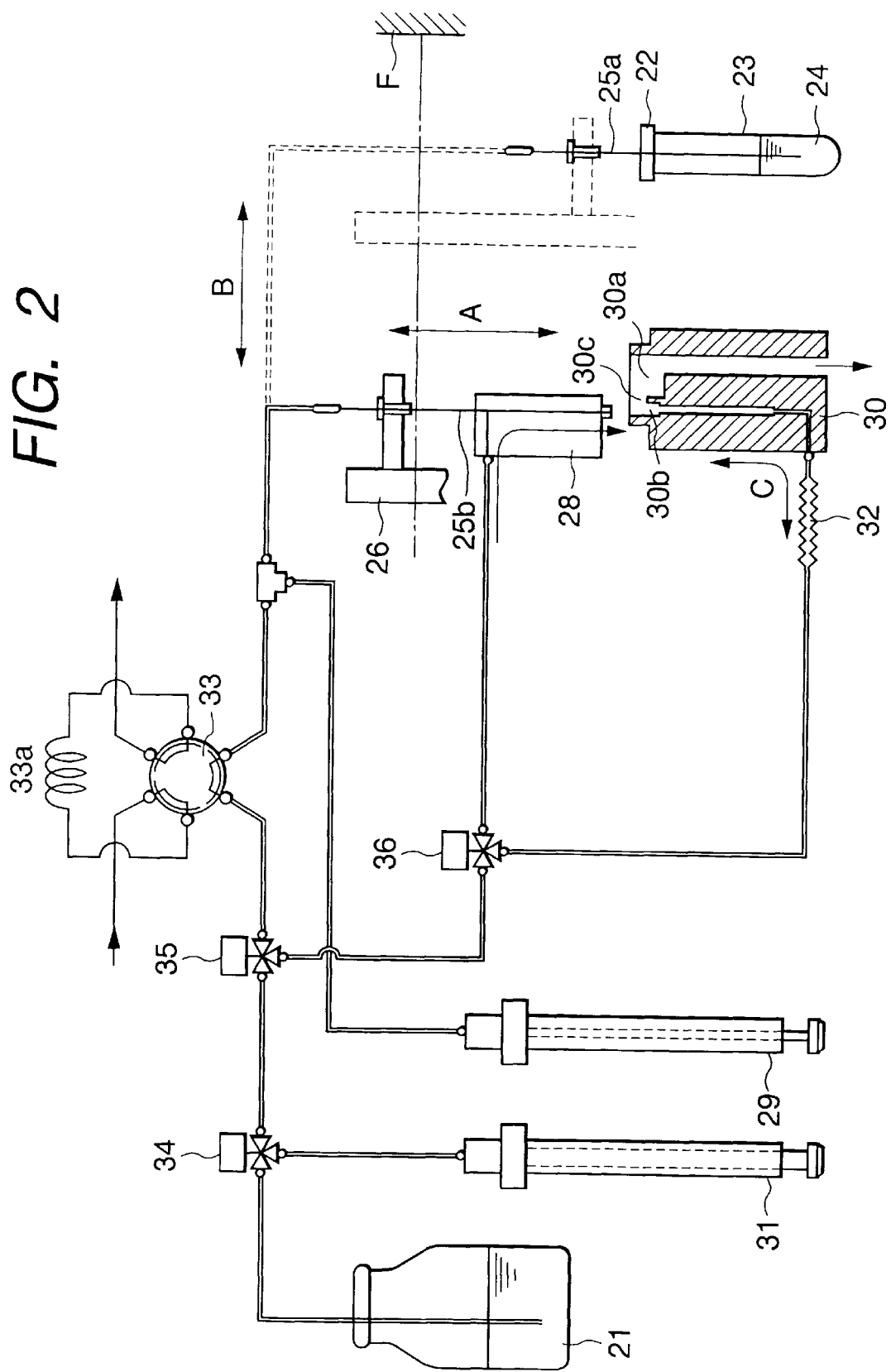
FIG. 2 is a diagram showing an analyzing apparatus according to the present invention and applied to a glycated-hemoglobin analyzing apparatus.

FIG. 2 is a diagram showing the structure of the present invention. The pretreatment apparatus according to the present invention is arranged to perform collection, dilution, mixture and washing of the components to prevent contamination as pretreatment. In order to perform the foregoing pretreatment, the present invention is arranged to use diluting solution for diluting the liquid sample and washing solution for washing components of the apparatus. Although the solution may be two or more types of solutions, sole type solution 21 may be employed, as shown in Fig. 2. That is, a glycated-hemoglobin analyzing apparatus is able to perform the dilution and the washing by a single type solution or the like having a salt concentration enabling red blood cells to be hemolyzed and containing a surface active agent for use in the washing operation. In the apparatus shown in FIG. 2, the washing and diluting solution 21 dilutes a blood sample 24 in a vacuum blood collecting tube 23 having a rubber cap 22. Moreover, the washing and diluting solution 21 has another function to serve as a solution for washing a needle 25 and so forth after the blood sample has been collected. In a case where low salt-concentration solution is used as the washing and diluting solution, simple use for diluting the blood sample cannot satisfactorily hemolyze the blood in general. However, satisfactory hemolysis can be realized by performing sufficient mixture which is performed in a mixing fluid passage to be described later.

The apparatus shown in FIG. 2 includes a fluid passage (a solution suction system) composed of a first syringe 31, a tank storing the diluting and washing solution 21, a first valve 34 and pipes for connecting the foregoing components, a fluid passage (a sampling system) composed of a sample injector 33 using a usual hexagonal injection valve, a needle 25, the first valve 34, a second valve 35 and pipes for connecting the foregoing components, a fluid passage (a needle washing system) composed of the first syringe 31, a needle washing block 28, the first valve 34, the second valve 35, a third valve 36 and pipes for connecting the foregoing components, a fluid passage (a mixing fluid passage system) composed of the first syringe 31, a mixing fluid passage 32, a diluting tank 30b, the first valve 34, the second valve 35, the third valve 36 and pipes for connecting the foregoing components and a system composed of a second syringe 29 for sucking the blood sample, the needle 25 and pipes for connecting the foregoing components. As described above, the structure of the present invention shown in FIG. 2 comprises the first syringe 31 for sucking and discharging the diluting and washing solution and the second syringe 29 for sucking and discharging the blood sample. However, a portion of the operation may be performed by a syringe provided additionally.

The apparatus according to the present invention shown in FIG. 2 is structured such that the syringe is operated prior to performing the actual pretreatment of the liquid sample to be described later. Moreover, each valve is switched to previously fill each system with the diluting and washing solution. However, it is preferable that the mixing fluid passage system be arranged such that an air layer be located adjacent to the diluting tank 30b to rearwards push the diluting and washing solution, with which the diluting tank 30b has been filled, to a position between the mixing fluid passage and the diluting tank by operating the first syringe so as to cause the diluted sample and the washing and diluting solution to be located while interposing the air layer.

Although the example shown in FIG. 2 has the structure such that the needle 25 is in the pin shape in order to penetrate the rubber cap 22 of the vacuum blood collecting tube 23, the length, the specific shape and so forth are not limited particularly.

The needle 25 is held by a needle holding mechanism 26 so as to be capable of moving vertically in the perpendicular direction indicated by symbol A shown in the drawing. The needle holding mechanism 26 is supported by a frame F so as to be capable of moving in a horizontal direction indicated by symbol B in the drawing. A needle washing block 28 is attached to the needle holding mechanism 26. That is, the needle 25, structured to penetrate the needle washing block 28 and to be capable of moving in the vertical direction, does not vertically move. Therefore, the vertical movement of the needle 25 causes the relative positional relationship with the needle washing block 28 to be changed.

The needle 25 is, attributable to the horizontal directional (in the direction B) movement of the frame, moved to a position above a position at which the blood sample 24 is sampled from the vacuum blood collecting tube 23. At this position, the needle holding mechanism 26 is moved downwards (in the direction A) so that the needle 25 penetrates the rubber cap 22 so as to be submerged into the blood sample 24 (in a state 25a). When the second syringe 29 is operated in the foregoing state, a blood sample is sucked in a predetermined quantity. When the glycated-hemoglobin analysis is performed, the quantity of suction is usually about 3 microliter.

After the blood sample has been sucked, the movements of the needle holding mechanism 26 and the frame cause the needle 25 to be moved to a position above the solution discharge tank 30a of the pretreatment tank 30 formed by integrating the diluting tank 30b for diluting the liquid sample and the solution discharge tank 30a for discharging the waste solution so as to wash the outer surface of the needle. At the foregoing position, the valves 34, 35 and 36 in the passage formed from the first syringe 31 to the needle washing block 28 are opened to open the needle washing system so as to supply the diluting and washing solution 21 to the needle washing block 28 in order to wash the outer surface of the needle 25. The needle washing block 28 is a block for permitting the needle to penetrate and having a columnar hollow portion formed in the vertical direction, the columnar hollow portion having an inner diameter somewhat larger than the outer diameter of the needle. The hollow portion is communicated with a passage for introducing the washing solution formed in the side surface of the upper portion of the block. The passage for introducing the washing solution is communicated with the first syringe 31 through the valve. When the needle washing system is opened, the diluting and washing solution 21 is introduced into the needle washing passage from the introduction passage to flow along the outer surface of the needle 25 and then abolished into the solution discharge tank 30a after it has washed the outer surface. As a result of the above-mentioned structure, any special suction pump for discharging the sample is not required to discharge the contaminated diluting and washing solution because the contaminated diluting and washing solution can be discharged by the gravity itself. As a matter of course, the solution discharge tank 30a may be connected to a pump or the like through a vacuum chamber or the like.

The needle washing passage, which is a fluid passage for the diluting and washing solution for washing the needle, is also a guide for holing the needle 25 penetrating the needle washing block 28 to guide the vertical movement of the needle 25. Therefore, it is preferable that the length of the passage be as long as possible. However, as described later, the length may be arbitrarily determined in consideration of the range for the vertical movement because the needle 25 is vertically moved when the needle is washed.

The top end of the needle washing passage formed in the vertical direction of the needle washing block 28 is sealed by a sealing member, such as an O-ring. The structure of the passage is formed such that overflow from the upper portion can be prevented when the diluting and washing solution has been supplied to cause the solution to be discharged through only the lower end opening. The sealing member, such as the O-ring, does not restrain the vertical movement of the needle 25. The sealing member has an effect of wiping out abrasion dust of the rubber cap allowed to adhere to the outer surface of the needle 25 when the needle is vertically moved in the above-mentioned state. It is preferable that the foregoing vertical movement be performed about three times. It is most preferable that the width of the movement be determined such that the overall body of the needle comes in contact with the O-ring or the like. At least the portion which has penetrated the rubber cap is required to be in contact as described above. To cause the diluting and washing solution to be satisfactorily supplied to the outer surface of the needle, it is preferable that the passage for introducing the diluting and washing solution be formed perpendicular to the needle washing passage. Moreover, it is preferable that the inner diameter of the passage for introducing the diluting and washing solution be smaller than the inner diameter of the needle washing passage.

As described above, the needle 25, having the outer surface which has been washed such that the needle 25 is vertically moved several times while allowing the diluting and washing solution to flow above the solution discharge tank 30a of the pretreatment tank 30 formed by integrating the diluting tank for diluting the liquid sample and the solution discharge tank, is horizontally moved to a position above the diluting tank 30b of the pretreatment tank 30, and then moved downwards to the bottom portion of the diluting tank 30b. At the foregoing position, the system from the second syringe 29 to the needle 25 is opened to discharge the overall quantity of the blood sample sucked into the needle. Then, the valve is switched to open the sampling system from the first syringe 31 to the needle 25 so as to slowly discharge the diluting and washing solution 21 in accordance with the dilution ratio. If the capacity of the diluting tank 30b is not smaller than the quantity of the sample to be actually analyzed, the capacity is not required to be larger than the capacity of the diluted sample realized by the dilution. The height of partition 30c between the diluting tank 30b and the solution discharge tank 30a formed integrally is reduced. Thus, the diluted sample allowed to flow over the partition 30c is introduced into the solution discharge tank 30a. Note that the diluted sample allowed to flow over into the solution discharge tank 30a can be discharged by only the gravity.

As can be understood from the drawing, the diluting tank 30b has a structure such that the cross sectional area in the horizontal direction is enlarged in a direction from the bottom portion to the upper end. Although the shape of the diluting tank 30b may be tapered (a conical shape) to realize continuous change in the cross sectional area, the shape may be changed in, for example, three stepped manner as illustrated (as a shape formed by combining columns having the three different cross sectional areas are combined). As a result of the above-mentioned structure, a problem can be prevented in which diffusion of the blood sample into the diluting and washing solution is insufficient to therefore cause the concentration gradient takes place after the dilution and the relative high concentration portion to be missed due to overflow into the solution discharge tank 30a. Since the diluted sample is again sucked by the needle 25 as described above, it is preferable that the inner diameter of the bottom portion to permit the leading end portion of the needle 25 to reach the bottom portion.

According to the knowledge obtained by the inventor of the present invention, the bottom portion of the diluting tank 30b is in a circular shape having a cross sectional area which is larger than the outer diameter of the needle by about 0.5 mm to about 1.5 mm in order to permit the following needle 25 to satisfactorily suck the diluted sample. It is further preferable that a tapered shape be employed, the diameter of which is reduced in a direction toward the leading end as shown in FIG. 3. It is preferable that the portion adjacent to the top end is about four to about six times the cross sectional area of the bottom portion in order to realize a satisfactory diffusion state when the dilution is performed.

Then, the valves 34, 35 and 36 are switched to open the mixing fluid passage system formed from the first syringe 31 to the lower end of the diluting tank 30b of the pretreatment tank 30. Then, the first syringe 31 is reciprocated so as to reciprocate the diluted sample in the fluid passage indicated by symbol C in the drawing. As can be understood from the drawing, the pipes adjacent to the diluting tank 30b in the mixing fluid passage are formed into a special mixing fluid passage 32 in which a plurality of portions having different cross sectional areas are continued. The mixing fluid passage 32 changes the flow rate when the diluted sample passes through the mixing fluid passage 32 to generate an arbitrary turbulent flow so as to improve the mixing efficiency so as to satisfactorily hemolyze the blood sample. The shape of the mixing fluid passage is not limited to that shown in the drawing. If the employed shape has changes in the cross sectional area to change the flow rate of the passing solution to generate the turbulent flow, the shape is not limited. It is preferable that the fluid passage has the same capacity as that of the diluting tank 30b or a capacity larger than the capacity of the same. The diluted sample mixed in the mixing fluid passage is finally returned to the diluting tank. Note that in the mixing fluid passage System, the diluting and washing solution and the diluted sample are located while interposing the air layer. Although it is preferable that the needle be located in the diluting tank 30b during the operation using the mixing fluid passage system, it may temporarily be moved to, for example, a position above the diluting tank 30b.

After the diluted sample has been mixed in the mixing fluid passage system, the overall quantity of the diluted sample returned to the diluting tank 30b is sucked by opening the sampling system formed from the first syringe 31 to the needle 25 and by operating the first syringe 31. As can be understood from also the drawing, a general type sample injector 33 using the hexagonal injection valve is disposed in the sampling system formed from the first syringe 31 to the needle 25. Thus, a predetermined quantity of the diluted sample sucked by the needle 25 is received in a sample loop 33a in the sample injector 33. If the capacity of the fluid passage formed from the needle 25 to the sample loop 33a is larger than the capacity of the diluting tank 30b, the needle 25 may temporarily be moved to, for example, a position above the diluting tank 30b in order to take air following the diluted sample. In particular, it is preferable that the capacity of the fluid passage which reaches the sample loop 33a be substantially the same as the capacity of the diluting tank 30b. More preferably, the capacity of the fluid passage which reaches the second valve 35 is made to be substantially the same as the capacity of the diluting tank 30b so as to locate the sample loop 33a at the intermediate position in view of the capacity.

After the overall quantity of the diluted sample has been sucked by the needle 25, the mixing fluid passage system is opened in a state where the leading end of the needle is located in the bottom portion of the dilution tank. Then, the first syringe is operated to discharge the diluting and washing solution so as to wash the dilution tank and the mixing fluid passage. As a result of the washing operation, also the diluted sample allowed to adhere to the outer surface of the needle can be washed. The quantity of discharge of the diluting and washing solution is made to be larger than the capacity of the diluting tank 30b. Moreover, the operation is performed to cause the diluting and washing solution to flow over into the solution discharge tank 30a. Then, the first syringe is operated to rearwards push the diluting and washing solution left in the dilution layer to a position between the mixing fluid passage and the dilution tank. Thus, when a next pretreatment is performed, the diluted sample and the washing and diluting solution are located while interposing the air layer.

As a final step of the pretreatment operation, the needle 25 is moved from the diluting tank 30b to a position above the solution discharge tank 30a. Then, the sampling system is opened, and then the first syringe 31 is operated to discharge the diluting and washing solution so as to abolish the diluted sample left in the sampling system. As a result, washing of the sampling system including the inside portion of the needle can be completed. Therefore, the diluted sample or the like left in the sampling system does not generate contamination when the next sampling operation is performed.

Note that the diluted sample received in the sample loop 33a is supplied to a glycated-hemoglobin analyzing column filled with positive ion exchange resin (not shown).

A structure in which the present invention is applied as a pretreatment apparatus of a glycated hemoglobin analyzing apparatus will now be described with reference to an example. Note that the present invention is not limited to the structure of the example.

In general, the pretreatment apparatus for the glycated hemoglobin analyzing apparatus must satisfy time required to complete the pretreatment being 120 seconds or shorter, carry (contamination) from the previous blood sample being 1% or smaller, the dilution ratio being about 250 times and reproducibility (CV) being 10% or lower. Moreover, the apparatus is required to perform the dilution and hemolysis of red blood cells.

The overall structure of the employed pretreatment apparatus is as shown in FIG. 2. As the diluting and washing solution 21, a marketing hemolyzing agent for glycated-hemoglobin analysis (hemolyzing agent C manufactured by Tosoh Corporation) was employed. As the blood sample 24, blood was employed, to which EDTA was added as a blood coagulation preventive agent, which was collected into the vacuum blood collecting tube 23 having the rubber cap 22, subjected to centrifugal sedimentation at 3000 rpm for 10 minutes and allowed to stand for three days to have high viscosity.

As the first syringe 31 for sucking and discharging the solution, a syringe having a capacity of 2500 microliter was employed. As the second syringe 29 for sucking and discharging the sample, a syringe having a capacity of 250 microliter was employed. Each of the first valve 34, the second valve 35 and the third valve 36 was a marketing three-way electromagnetic vale (manufactured by Advance Electric Company Inc.). As the sample injector 33, a marketing hexagonal injection valve (manufactured by Rheodyne Incorporated) was employed. Note that the capacity of the sample loop 33a of the sample injector was 10 microliter.

As the needle 25, a needle having an outer diameter of 1.25 mm, a length of 15.5 cm and having an opening, the diameter of which was 0.6 mm and which was formed at a position distant from the leading end of the needle for a distance of 4.2 mm was employed. As the mixing fluid passage connected to the dilution tank 33b, a passage was employed which was made of a Teflon tube having an inner diameter of 2 mm and a length of 20 cm and a portion of which was reduced in the diameter to have a wavy cross sectional shape.

As the pretreatment tank 30 formed by integrating the dilution tank for diluting the liquid sample and the solution discharge tank, a tank made of PMMA (acrylic resin) was employed. The overall shape of the pretreatment tank is shown in FIG. 3a, and the detailed structure of the diluting tank 30b is shown in FIG. 3b.

The area of the opening in the solution discharge tank 30a was 112.26 mm². The axial line of the hole in the dilution tank and the axial line of the hole in the solution discharge tank were apart from each other for 14 mm. The overall length (a) of the diluting tank 30b was 47 mm. The hole was in the form of a columnar shape having the cross sectional area changed in three steps such that it was in the form of a columnar shape having an inner diameter of 2.5 mm in a region from the bottom surface to a position of 7 mm, a columnar shape having an inner diameter of 3 mm in a region from the position of 7 mm apart from the bottom surface to a position of 43 mm and a columnar shape having an inner diameter of 5 mm in a region from the position of 43 mm apart from the bottom surface to a position of 47 mm. The capacity was 367.18 microliter. The capacity which was realized when the needle was moved downwards to the bottom surface of the dilution tank was about 310 microliter which was a value obtained by subtracting the capacity of the needle. The height (b) of the outer portion of the dilution tank was 4.5 mm. Since the height of the partition from the solution discharge tank was the same as the height of the top end of the dilution tank and the width (c) was made to be 1 mm, the diluted sample allowed to flow over the dilution tank was introduced into the solution discharge tank to prevent discharge from the pretreatment tank to the outside.

The needle washing block 28 has the structure such that a block having an overall length of 40 mm, a width of 20 mm and a depth of 40 mm and made of PMMA (acrylic resin) was provided with a columnar hole serving as the needle washing passage having an inner diameter of 1.8 mm and an overall length of 40 mm. A washing solution introducing passage was formed at a position of 5 mm apart from the top end of the needle washing passage, the washing solution introducing passage being connected perpendicularly to the needle washing passage and having an inner diameter of 0.8 mm. Moreover, an O-ring serving as the sealing member and having an inner diameter of 1.2 mm was secured to the opening at the top end of the needle washing passage. In addition, a cylindrical nozzle having a hollow portion, the inner diameter of which was 1.8 mm and a length of which was 5 mm, was secured to the lower end to cause the washing solution to easily be abolished to the solution discharge tank 30a.

The pipes except the mixing fluid passage 32 were Teflon pipes each having an inner diameter of 0.8 mm.

The quantity of the blood sample to be collected by the needle was 3 microliter. The washing and diluting solution in a quantity of 600 microliter was discharged into the dilution tank at a discharge rate of 131 microliter/second. Since the capacity of the dilution tank was 310 microliter, 290 microliter flowed over into the solution discharge tank 30a. The needle was washed such that the diluting and washing solution in a quantity of 900 microliter was used while vertically reciprocating the needle three times. The dilution tank and the mixing fluid passage having the total capacity of 367.18 microliter were washed by discharging the diluting and washing solution in a quantity of 1342 microliter.

The operation for mixing the diluted sample in the mixing fluid passage was performed by reciprocating the first syringe to reciprocate the diluted sample in the fluid passage three times. The blood sample subjected to the pretreatment was supplied to a column filled with the positive ion exchange resin by the sample injector, and then excessive diluted sample was discharged from the needle into the solution discharge tank. Then, the diluting and washing solution in a quantity of 300 microliter was jetted out to wash the inside portions of the pipes in the sampling system and the needle.

The foregoing operation took time of about 110 seconds. The pretreatment apparatus according to the present invention was able to satisfactorily perform the pretreatment operation, particularly the mixing operation. As a result, blood cells were sufficiently hemolyzed. Therefore, the analysis was resulted satisfactorily. After the pretreatment was performed, a liquid sample containing no glycated-hemoglobin component was employed to perform a similar pretreatment operation. As a result, substantially no chromatogram peak considered to be a residue (contamination) of the pervious blood sample was observed. The area of the chromatogram indicating the absolute value of the obtained blood cells was substantially the same as that realized by performing manual pretreatment (dilution) by 250 times.

As a result of observations of reproducibility of the pretreatments (dilution) with the same blood cells, the reproducibility (CV) obtained after conducting the pretreatment operations of ten (10) times was 1.26%; CV=1.26%.

The glycated hemoglobin analyzing apparatus having the above-mentioned pretreatment apparatus according to the present invention was used to analyze 8000 blood samples collected into the vacuum blood collecting tube. As a result, dust of the rubber cap allowed to adhere to the needle was abolished into the solution discharge tank. Thus, no contamination (contaminant) was confirmed in the dilution tank. Moreover, any problem of clogging or the like did not arise.

The pretreatment apparatus according to the present invention has the structure such that when the diluted sample which has diluted the liquid sample, such as blood, is larger than the capacity of the dilution tank, the portion exceeding the foregoing capacity is caused to flow over into the solution discharge tank so as to be abolished. When usual glycated-hemoglobin analysis must dilute the blood sample by 200 times to 400 times. On the other hand the quantity of the blood sample to be collected cannot be made to be 3 microliter or smaller to obtain satisfactory reproducibility. As a result, if the overall quantity of the diluted sample is stored, the capacity of the dilution tank is enlarged, causing the washing solution to be required in a large quantity to wash the dilution tank. What is worse, the diffusion and mixture of the blood sample in the dilution tank are frequently insufficient. On the other hand, the present invention has the structure such that the capacity of the dilution tank is positively made to be small and the diluted sample allowed to flow over the dilution tank is used to perform primary washing of the dilution tank.

As described above, the capacity of the dilution tank is reduced so that present invention is able to reduce the quantity of the washing solution required to wash the dilution tank. Moreover, the present invention has the contrivance in the shape of the dilution tank such that the mixing fluid passage is formed in the dilution tank. Thus, diffusion and mixture of the liquid sample or the like in the dilution tank can efficiently be performed in a short time. As a result of the foregoing structure, efficient dilution and mixture can be performed with the glycated-hemoglobin analyzing apparatus which uses a blood sample as the liquid sample. In this case, another effect can be obtained in that hemolysis of the blood sample can be realized. If the number of the reciprocating operations is adjusted by changing the operation times of the syringe, the degree of mixture adaptable to the type of the liquid sample can easily be realized.

According to the present invention, the pretreatment, such as the washing of the needle, the dilution tank and the mixing fluid passage, can be performed by a single syringe and the three valves for switching the system as illustrated. Thus, the apparatus can be simplified and the time required to perform the pretreatment can be shortened.

According to the present invention, the columnar hole serving as the dilution tank can be washed with the washing solution discharged from the syringe. Moreover, the washing solution discharged in a quantity larger than the capacity of the dilution tank flows over in the adjacent solution discharge tank so that contamination occurring attributable to contaminant in the top end of the dilution tank is effectively prevented. In addition, elements, such as the suction pump, the vacuum chamber, the exclusive valves for only washing the dilution tank of the conventional apparatus are not required. Since the top end of the dilution tank is not contaminated because the washing solution is allowed to flow over the dilution tank, the dilution tank can be formed into a maintenance-free structure.

According to the present invention, also the needle for collecting the liquid sample, such as blood, can sufficiently be washed. Since the sealing member, such as the O-ring, attached to the needle washing block causes the washing solution to flow along the needle while wiping out the abrasion dust of the rubber cap allowed to adhere to the needle, the outer surface of the needle can be washed. Therefore, the abrasion dust of the rubber cap and so forth are abolished into the solution discharge tank. Therefore, another effect can be obtained in that probability of introduction of the dust into the pipes in the apparatus and generation of clogging can be eliminated satisfactorily.

What is claimed is:

1. A pretreatment apparatus for distributing a washing solution, comprising:

a needle for sampling a liquid sample in a predetermined quantity;

a needle holding mechanism for movably holding said needle;

a pretreatment tank having a diluting tank, a liquid discharge tank integrally formed therewith, and a partition interposed between said diluting and said liquid discharge tanks, said diluting tank for receiving the predetermined quantity of the liquid sample and a diluting solution to form a diluted liquid sample, said liquid discharge tank for discharging waste liquid, said partition for introducing one of said diluted liquid sample and said washing solution flowing over said partition into said solution discharge tank, said diluting tank having an inlet for passing one of said washing solution and said diluted liquid sample into said diluting tank;

a mixing fluid passage, for mixing the diluted liquid sample, extending from said inlet; and pipes and two syringes defining flow passages connecting said needle and said mixing fluid passage.

2. The pretreatment apparatus according to claim 1, wherein said washing solution and said diluting solution are one in the same.

3. The pretreatment apparatus according to claim 1, wherein said needle holding mechanism is moveable in a vertical direction, and said pretreatment apparatus further includes a frame for movably holding said needle holding mechanism in a horizontal direction.

4. The pretreatment apparatus according to claim 3, further including:

a needle washing block provided for said needle holding mechanism, and moveable in the horizontal direction together with said needle, but not moveable in the vertical direction, said needle washing block including a bore through which said needle extends, and a washing inlet communicating with said bore;

wherein one of said pipes connects to said washing inlet to provide said washing fluid into said bore.

5. The pretreatment apparatus according to claim 1, wherein said pretreatment apparatus is a pretreatment portion of a glycated-hemoglobin analyzing apparatus.

6. The pretreatment apparatus according to claim 1, wherein said diluting tank has a horizontal cross sectional area which increases from a bottom portion to an upper end thereof.

7. The pretreatment apparatus according to claim 1, wherein said mixing fluid passage includes a plurality of portions having different cross sectional areas connected in series.

* * * * *